(12) United States Patent
Lee et al.

(10) Patent No.: US 11,101,424 B2
(45) Date of Patent: Aug. 24, 2021

(54) ULTRASOUND TRANSDUCER AND MANUFACTURING METHOD THEREOF

(71) Applicant: Siemens Medical Solutions USA, Inc., Malvern, PA (US)

(72) Inventors: KyungHo Lee, Pohang-si (KR); YoungShin Kim, PoHang-si (KR); Baik Woo Lee, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 505 days.

(21) Appl. No.: 16/100,279

(22) Filed: Aug. 10, 2018

(65) Prior Publication Data

US 2019/0088849 A1 Mar. 21, 2019

(30) Foreign Application Priority Data

Sep. 15, 2017 (KR) .......................... 10-2017-0118378

(51) Int. Cl.
*H01L 41/047* (2006.01)
*B06B 1/02* (2006.01)
(Continued)

(52) U.S. Cl.
CPC ........ *H01L 41/0475* (2013.01); *B06B 1/0215* (2013.01); *B06B 1/0622* (2013.01);
(Continued)

(58) Field of Classification Search
CPC ............... H01L 41/0475; H01L 41/338; H01L 41/0825; H01L 41/29; B06B 1/0215; B06B 1/0622; A61B 8/4444
See application file for complete search history.

(56) References Cited

U.S. PATENT DOCUMENTS 8,803,404 B2 * 8/2014 Kwon .................. B06B 1/0622
310/334
2001/0041837 A1 * 11/2001 Takeuchi ................ H01L 41/37
600/437
(Continued)

FOREIGN PATENT DOCUMENTS

CN 10138553 3/2009
CN 104889042 9/2015
(Continued)

OTHER PUBLICATIONS

Korean Patent Application No. 2014-0131414, filed Sep. 30, 2014, with English translation of claims and abstract.
(Continued)

*Primary Examiner* — Bryan P Gordon

(57) ABSTRACT

An ultrasound transducer used in an ultrasound system and a method of manufacturing the same are disclosed. The ultrasound transducer is manufactured by forming a backing block including a plurality of surfaces; forming a piezoelectric layer including a first portion formed on the backing block to be in contact therewith and a second portion extending from the first portion; electrically connecting a plurality of pins to the second portion by attaching a connector having the plurality of pins for electrical connection with at least one of a transmitting unit and a receiving unit of an ultrasound system to at least one surface of the plurality of surfaces of the backing block; cutting the first portion and the second portion of the piezoelectric layer into a plurality of piezoelectric elements, wherein each of the plurality of piezoelectric elements is connected to a corresponding one of the plurality of pins of the connector; and forming a ground layer connected to the piezoelectric layer.

16 Claims, 5 Drawing Sheets

(51) Int. Cl.
*B06B 1/06* (2006.01)
*H01L 41/04* (2006.01)
*H01L 41/338* (2013.01)
*H01L 41/29* (2013.01)
*H01L 41/08* (2006.01)
*A61B 8/00* (2006.01)

(52) U.S. Cl.
CPC ........ *H01L 41/042* (2013.01); *H01L 41/0825* (2013.01); *H01L 41/29* (2013.01); *H01L 41/338* (2013.01); *A61B 8/4444* (2013.01); *B06B 2201/76* (2013.01)

(56) References Cited

U.S. PATENT DOCUMENTS

| | | | |
|---|---|---|---|
| 2009/0034370 A1* | 2/2009 | Guo | H04R 31/00 367/180 |
| 2010/0066207 A1* | 3/2010 | Saito | A61B 8/4281 310/335 |
| 2013/0045611 A1 | 2/2013 | MacDougall | |
| 2013/0134834 A1* | 5/2013 | Yoshikawa | H01L 41/053 310/341 |
| 2018/0033945 A1 | 2/2018 | Kim et al. | |

FOREIGN PATENT DOCUMENTS

| | | |
|---|---|---|
| CN | 105127082 | 12/2015 |
| EP | 2908553 | 8/2015 |
| JP | 2512209 | 7/1996 |
| JP | H10327498 | 12/1998 |
| WO | 2016137737 | 9/2016 |

OTHER PUBLICATIONS

Korean Patent Application No. 2015-0008160, filed Jan. 16, 2015, with English translation of claims and abstract.

English translation of Korean Patent Application No. 2016-0173521, filed Dec. 19, 2016.

* cited by examiner

ULTRASOUND TRANSDUCER AND MANUFACTURING METHOD THEREOF

BACKGROUND

The present disclosure relates to an ultrasound transducer used in an ultrasound system and a manufacturing method thereof.

SUMMARY

Ultrasound systems have been widely used in the medical field for obtaining information about objects of interest inside a target object due to their non-invasive and non-destructive characteristics. Such ultrasound systems can provide high-resolution images of the target object in real time using a high-frequency sound wave, without a need for a surgical operation in which an incision is made directly in the target object.

An ultrasound system includes an ultrasound transducer for generating ultrasound signals and transmitting and receiving the generated ultrasound signals. The ultrasound transducer includes a piezoelectric layer formed of a piezoelectric ceramic element such as Lead Zirconate Titanate (PZT) to generate an ultrasound signal in response to an electrical pulse signal and transmit the generated ultrasound signal into a target object. In addition, the ultrasound transducer is configured to receive an echo signal reflected from a target object, convert the received echo signal into an electrical signal, and transmit the electrical signal to an ultrasound imaging device.

The piezoelectric layer in the ultrasound transducer is disposed between a backing block and an acoustic matching layer. Such a backing block is made of a material having a high damping coefficient and an impedance value similar to the acoustic impedance of the piezoelectric ceramic element. In addition, when an electrical pulse signal is applied to the piezoelectric ceramic element, the backing block suppresses vibration of the piezoelectric ceramic element and facilitates generating an ultrasound signal having a short pulse. Further, the backing block serves to reduce the heat of the piezoelectric ceramic element and absorb an ultrasound signal generated on the rear surface side of the piezoelectric ceramic element.

Since a Flexible Printed Circuit Board (FPCB) for processing a signal and a flexible circuit board for grounding are generally required in order to drive the piezoelectric layer, the wiring structure of the ultrasound transducer is complicated and the cost of manufacturing the ultrasound transducer is increased.

The present disclosure provides an ultrasound transducer formed by attaching, to a backing block, a connector connected to a cable extending from an ultrasound system, and a method of manufacturing the ultrasound transducer.

According to an aspect of the present disclosure, a method of manufacturing an ultrasound transducer includes: forming a backing block including a plurality of surfaces; forming a piezoelectric layer including a first portion formed on the backing block to be in contact therewith and a second portion extending from the first portion; electrically connecting a plurality of pins to the second portion by attaching a connector having the plurality of pins for electrical connection with at least one of a transmitting unit or a receiving unit of an ultrasound system to at least one surface of the plurality of surfaces of the backing block; cutting the first portion and the second portion of the piezoelectric layer into a plurality of piezoelectric elements, wherein each of the plurality of piezoelectric elements is connected to a corresponding one of the plurality of pins of the connector; and forming a ground layer connected to the piezoelectric layer.

Further, in the method of manufacturing an ultrasound transducer according to one aspect of the present disclosure, electrically connecting the plurality of pins to the second portion includes electrically connecting the plurality of pins of the connector to the second portion of the piezoelectric layer by attaching at least one conductive paste selected from among a solder paste, an epoxy adhesive, and a silver epoxy between the second portion and the plurality of pins.

Further, in the method of manufacturing an ultrasound transducer according to one aspect of the present disclosure, cutting the first portion and the second portion of the piezoelectric layer into the plurality of piezoelectric elements includes simultaneously cutting the conductive paste attached between the second portion and the plurality of pins when cutting the first portion and the second portion of the piezoelectric layer into the plurality of piezoelectric elements.

Further, in the method of manufacturing an ultrasound transducer according to one aspect of the present disclosure, cutting the first portion and the second portion of the piezoelectric layer into the plurality of piezoelectric elements includes inserting an insulating material between each pair of the adjacent piezoelectric elements.

Further, in the method of manufacturing an ultrasound transducer according to one aspect of the present disclosure, the second portion protrudes from the first portion by a length greater than or equal to a height of the plurality of pins of the connector.

Further, in the method of manufacturing an ultrasound transducer according to one aspect of the present disclosure, forming the backing block includes forming a ground region on one or more surfaces of the backing block for connecting to the ground layer.

Further, in the method of manufacturing an ultrasound transducer according to one aspect of the present disclosure, forming the ground layer connected to the piezoelectric layer includes forming the ground layer on the piezoelectric layer.

Further, in the method of manufacturing an ultrasound transducer according to one aspect of the present disclosure, forming the ground layer connected to the piezoelectric layer includes attaching a ground connector configured to perform a grounding function to at least one of the surfaces of the backing block that is different from the surface to which the connector is attached, and connecting the ground layer and the ground connector.

According to another aspect of the present disclosure, an ultrasound transducer includes: a backing block including a plurality of surfaces; a piezoelectric layer including a first portion formed on the backing block to be in contact therewith and a second portion extending from the first portion; a connector having a plurality of pins for electrically connecting to at least one of a transmitting unit or a receiving unit of an ultrasound system, the connector being attached to at least one surface of the plurality of surfaces of the backing block and the plurality of pins being configured to electrically connect to the second portion; and a ground layer configured to be connected to the piezoelectric layer, wherein the piezoelectric layer includes a plurality of piezoelectric elements that are cut in the first portion and the second portion, and each of the plurality of piezoelectric elements is connected to a corresponding one of the plurality of pins of the connector.

Further, in the ultrasound transducer according to one aspect of the present disclosure, at least one conductive paste selected from among a solder paste, an epoxy adhesive, and a silver epoxy is attached between the second portion and the plurality of pins, so that the plurality of pins of the connector is electrically connected to the second portion of the piezoelectric layer.

Further, in the ultrasound transducer according to one aspect of the present disclosure, the conductive paste attached between the second portion and the plurality of pins is cut simultaneously with cutting the first portion and the second portion of the piezoelectric layer into the plurality of piezoelectric elements.

Further, in the ultrasound transducer according to one aspect of the present disclosure, an insulating material is disposed between each pair of the adjacent piezoelectric elements.

Further, in the ultrasound transducer according to one aspect of the present disclosure, the second portion protrudes from the first portion by a length greater than or equal to a height of the plurality of pins of the connector.

Further, in the ultrasound transducer according to one aspect of the present disclosure, the backing block includes a ground region formed on one or more surfaces of the backing block and configured to be connected to the ground layer.

Further, in the ultrasound transducer according to one aspect of the present disclosure, the ground region includes a ground connector configured to perform a grounding function and attached to one of the surfaces of the backing block that is different from the surface to which the connector is attached.

Further, in the ultrasound transducer according to one aspect of the present disclosure, the ground layer is formed on the piezoelectric layer.

According to embodiments of the present disclosure, since an ultrasound transducer may be manufactured without a Flexible Printed Circuit Board (FPCB) for processing a signal and a flexible circuit board for grounding to drive a piezoelectric layer, the wiring structure of the ultrasound transducer may be simplified and the cost of manufacturing the ultrasound transducer may be reduced by eliminating the expensive flexible circuit board.

DETAILED DESCRIPTION

Figure 1:
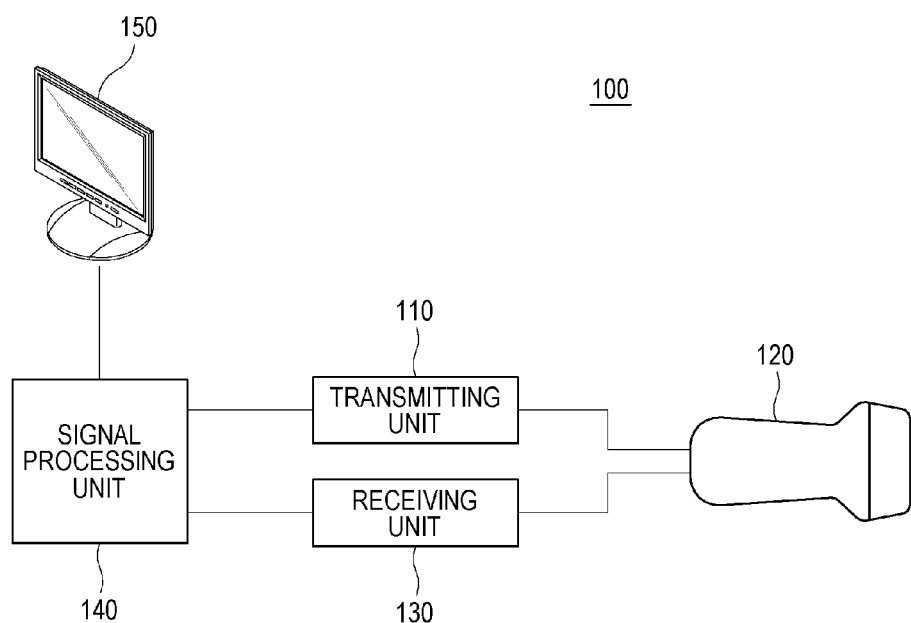
FIG. 1 is a block diagram schematically showing a configuration of an ultrasound system according to one embodiment of the present disclosure.

The embodiments of the present disclosure are illustrated for the purpose of describing the technical concepts of the present disclosure. The scope of the present disclosure is not limited to the embodiments described below or to the detailed description of these embodiments.

Unless otherwise defined, all technical and scientific terms used herein have the same meaning as commonly understood by one of ordinary skill in the art to which this invention belongs. All terms used in the present disclosure are chosen for the purpose of more clearly illustrating the disclosure and are not to be construed as limiting the scope of the present disclosure.

The terms "comprising," "including," and "having," and the like as used herein should be understood as open-ended terms connoting the possibility of inclusion of other embodiments, unless otherwise mentioned in a phrase or sentence including such terms.

A singular expression can include meanings of plurality, unless otherwise mentioned, and the same is applied to a singular expression stated in the claims.

The terms "first," "second," etc. used herein are used to identify a plurality of components from one another, and are not intended to limit the order or importance of the relevant components.

The term "unit" used in these embodiments means a software component or hardware component, such as a field-programmable gate array (FPGA) and an application specific integrated circuit (ASIC). However, a "unit" is not limited to software and hardware, and may be configured to be an addressable storage medium or may be configured to run on one or more processors. For example, a "unit" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "unit" may be combined into a smaller number of components and "units" or further subdivided into additional components and "units."

The expression "based on" used herein is used to describe one or more factors that influence a decision, an action of judgment or an operation described in a phrase or sentence including the relevant expression, and this expression does not exclude additional factor influencing the decision, the action of judgment or the operation.

When a certain component is described herein as "coupled to" or "connected to" another component, this should be understood as meaning that the certain component may be coupled or connected directly to the other component or that the certain component may be coupled or connected to the other component via a new intervening component.

Hereinafter, exemplary embodiments of the present invention will be described with reference to the accompanying drawings. In the accompanying drawings, identical or corresponding components are indicated by the same reference numerals. In the following description of the embodiments, repeated descriptions of identical or corresponding components may be omitted. However, even if a description of such components is omitted, such components are not intended to be excluded in an embodiment.

FIG. 1 is a block diagram schematically showing a configuration of an ultrasound system 100 according to one embodiment of the present disclosure.

As shown in FIG. 1, the ultrasound system 100 may include a transmitting unit 110, an ultrasound transducer 120, a receiving unit 130, a signal processing unit 140, and a display unit 150.

The transmitting unit 110 may time-delay an electrical pulse signal to have a predetermined transmitting pattern and transmit the time-delayed electrical pulse signal to the ultrasound transducer 120. The ultrasound transducer 120 includes an ultrasound transducer array having a plurality of transducer elements in which a plurality of matching layers is stacked on a piezoelectric ceramic element. The ultrasound transducer 120 may transmit an ultrasound beam to a target object in response to the time-delayed electrical pulse signal from the transmitting unit 110. Further, the ultrasound transducer 120 may receive an echo signal reflected from the target object, convert the echo signal into an electrical signal, and output a received signal. The receiving unit 130 applies a time delay to the received signal output from the ultrasound transducer 120 in consideration of a distance between each of the plurality of transducer elements of the ultrasound transducer 120 and a focal point, and then sums the time-delayed received signal to form a receive-focused beam.

The signal processing unit 140 may perform signal processing on the receive-focused beam to form ultrasound data, and may form an ultrasound image of the target object using the ultrasound data. Further, the signal processing unit 140 may control operations of the transmitting unit 110, the ultrasound transducer 120, and the receiving unit 130 for forming the ultrasound image. In one embodiment, the signal processing unit 140 may be implemented as a processor including a CPU, a microprocessor, a GPU, and the like, but is not limited thereto.

The display unit 150 may display the ultrasound image of the target object formed by the signal processing unit 140. Further, the display unit 150 may display a user interface for allowing a user to perform various measurements using the displayed ultrasound image. In one embodiment, the display unit 150 may include a Liquid Crystal Display (LCD), a Light Emitting Diode (LED) display, an Organic Light Emitting Diode (OLED) display, a flexible display, a Cathode Ray Tube (CRT) display, a Plasma Display Panel (PDP), and the like, but the display unit 150 is not limited thereto.

Figure 2:
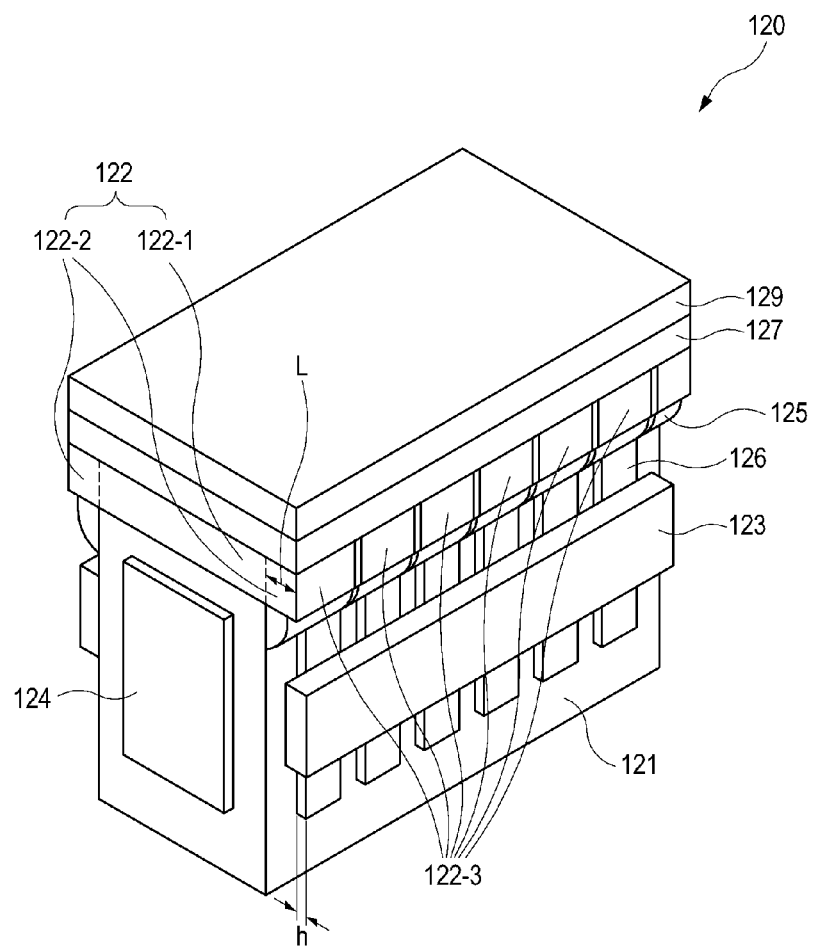
FIG. 2 is a perspective view showing an ultrasound transducer according to one embodiment of the present disclosure.

FIG. 2 is a perspective view of the ultrasound transducer 120 according to one embodiment of the present disclosure.

As shown in FIG. 2, the ultrasound transducer 120 may include a backing block 121, a piezoelectric layer 122, a connector 123, a ground region 124, a conductive paste 125, and a ground layer 127, and the connector 123 may include a plurality of pins 126.

The piezoelectric layer 122 is made of a piezoelectric ceramic element, and is configured to generate an ultrasound signal in response to an electrical pulse signal transmitted from the transmitting unit 110, receive an echo signal reflected from the target object, and convert the received echo signal into an electrical signal. In one embodiment, the piezoelectric layer 122 may include quartz crystal, piezoelectric ceramics sintered with barium titanate, Lead Zirconate Titanate (PZT), binary- and ternary-single crystal, dematching layer such as WC, and the like, but is not limited thereto. Further, the piezoelectric layer 122 may include a first portion 122-1 formed on the backing block 121 to be in contact therewith and a second portion 122-2 extending from the first portion 122-1. The second portion 122-2 may be electrically connected with the plurality of pins 126 included in the connector 123. In one embodiment, the second portion 122-2 may protrude from the first portion 122-1 by a length greater than or equal to a height of the plurality of pins 126 included in the connector 123. Here, the height of the plurality of pins 126 may indicate a height h of protrusion with respect to a surface on which the plurality of pins 126 is in contact with the backing block 121. For example, the second portion 122-2 may protrude to have a length L of 0.01 mm to 10 mm, but is not limited thereto. Further, at least one conductive paste 125 selected from among a solder paste, an epoxy adhesive, and a silver epoxy may be used for an electrical connection between the second portion 122-2 and the plurality of pins 126 included in the connector 123, but is not limited thereto.

Further, the first portion 122-1 and the second portion 122-2 of the piezoelectric layer 122 may be cut into a plurality of piezoelectric elements 122-3, and the plurality of piezoelectric elements 123 that have been cut may be connected one-to-one to the plurality of pins 126 of the connector 123. For example, the first portion 122-1 and the second portion 122-2 of the piezoelectric layer 122 may be cut into the plurality of piezoelectric elements 122-3 using a laser dicing device, a plasma cutting device, or the like, but are not limited thereto. In one embodiment, when the first portion 122-1 and the second portion 122-2 of the piezoelectric layer 122 are cut into the plurality of piezoelectric elements 122-3, the conductive paste 125 attached between the second portion 122-2 and the plurality of pins 126 may be cut simultaneously and even a part of the backing block 121 that is in contact with the conductive paste 125 and the first portion 122-1 may be cut simultaneously.

In addition, the first portion 122-1 and the second portion 122-2 of the piezoelectric layer 122 may be cut into the plurality of piezoelectric elements 122-3, and an insulator may be inserted between each pair of the adjacent piezoelectric elements 122-3 so that each of the plurality of piezoelectric elements 122-3 may be insulated. In one embodiment, the insulator disposed between the plurality of piezoelectric elements 122-3 may include mica, rubber, vinyl chloride, and the like, but is not limited thereto.

The backing block 121 including a plurality of surfaces is configured to rapidly suppress vibration of the plurality of piezoelectric elements 122-3 to generate an ultrasound signal having a short pulse when the electrical pulse signal transmitted from the transmitting unit 110 is applied to the plurality of piezoelectric elements 122-3 of the piezoelectric layer 122. Further, the backing block 121 may reduce the heat of the plurality of piezoelectric elements 122-3 and absorb the ultrasound signal generated on the side of the rear surface of the plurality of piezoelectric elements 122-3. Also, the connector 123 including the plurality of pins 126 may be attached to at least one surface of the plurality of surfaces of the backing block 121 so as to be electrically connected to the transmitting unit 110 and the receiving unit 130 of the ultrasound system 100.

Further, the backing block 121 may include the ground region 124 formed on one or more surfaces among the plurality of surfaces to allow the backing block 121 to be connected to the ground layer 127. In one embodiment, the ground region 124 may be formed by attaching a slab made of copper (Cu), gold (Au), silver (Ag), platinum (Pt), or the like to the backing block 121 using an epoxy adhesive.

The ground layer 127 may be formed to be connected to the first portion 122-1 or the second portion 122-2 of the piezoelectric layer 122 to ground the plurality of piezoelectric elements 122-3 included in the piezoelectric layer 122. In one embodiment, the ground layer 127 may be formed on the piezoelectric layer 122.

The matching layer 129 may be formed to reduce energy loss resulting from reflection of ultrasound signals due to an acoustic impedance difference between the piezoelectric layer 122 and a target object (e.g., a human body). In one embodiment, the matching layer 129 may be formed of a material having an acoustic impedance value corresponding to a value between those of the plurality of piezoelectric elements 122-3 of the piezoelectric layer 122 and the target object.

Figure 3:
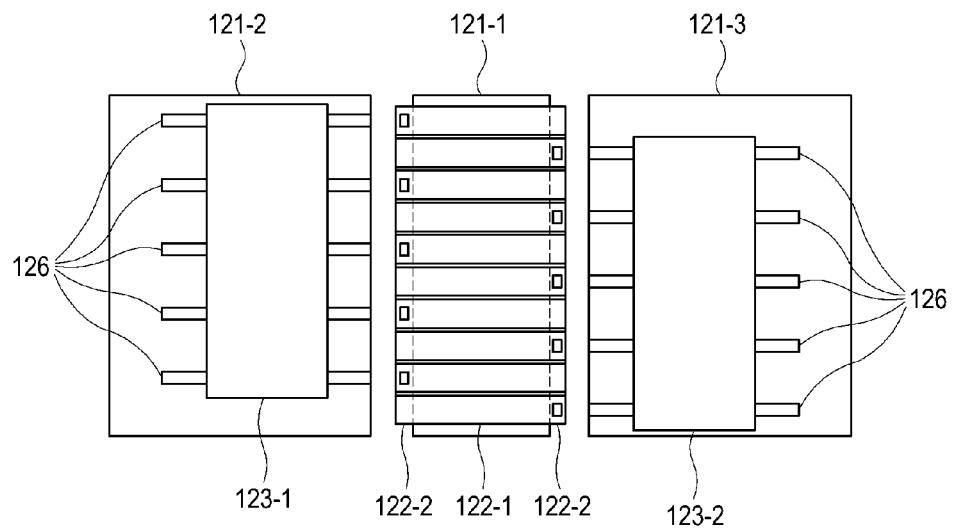
FIG. 3 is a planar figure showing an ultrasound transducer according to one embodiment of the present disclosure.

FIG. 3 is a planar figure showing an ultrasound transducer 120 according to one embodiment of the present disclosure.

As shown in FIG. 3, the ultrasound transducer 120 may include the backing block 121, the piezoelectric layer 122 and the connector 123. The connector 123 may include the plurality of pins 126, and may be disposed both sides 121-2, 121-3 of the backing block 121. The elements that perform the same functions as those of the ultrasound transducer 120 shown in FIG. 2 are denoted by the same reference numerals, and a detailed description thereof will be omitted.

The reference numeral 121-1 is a top view of the backing block 121 and the piezoelectric layer 122, the reference numeral 121-2 is a lateral view of the backing block 121 viewed from left side and the reference numeral 121-3 is a lateral view of the backing block 121 viewed from right side.

The pins 126 of the connector 123-1 attached left side of the backing block 121 and the connector 123-2 attached right side of the backing block 121 may be arranged in a zigzag shape. Thus, the number of pins 126 comprising each of connectors 123-1, 123-2 may be decreased and each distance between the pins 126 may be increased, compared to when the connector 123 is disposed only one side of the backing block 121 one of the left side 121-2 and the right side 121-3 of the backing block 121.

Figure 4:
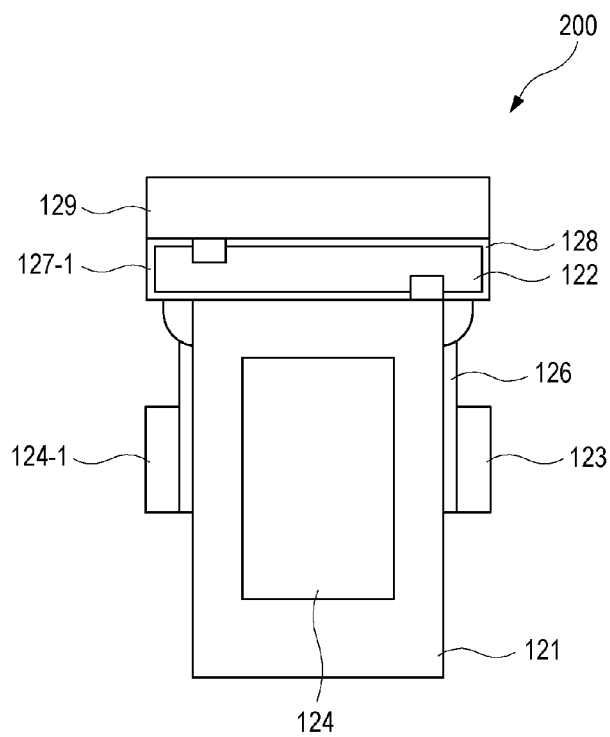
FIG. 4 is a front view showing an ultrasound transducer as viewed from one side according to an embodiment of the present disclosure.

FIG. 4 is a front view of an ultrasound transducer 200 viewed from one side according to an embodiment of the present disclosure.

As shown in FIG. 4, the ultrasound transducer 200 may include the backing block 121, the piezoelectric layer 122, the connector 123, a ground connector 124-1, a ground electrode 127-1, a signal electrode 128, and the matching layer 129, and the connector 123 may include the plurality of pins 126. The elements that perform the same functions as those of the ultrasound transducer 120 shown in FIG. 2 are denoted by the same reference numerals, and a detailed description thereof will be omitted.

The connector 123 including the plurality of pins 126 to be electrically connected to the transmitting unit 110 and the receiving unit 130 of the ultrasound system 100 may be attached to at least one of the plurality of surfaces of the backing block 121. Further, the ground connector 124-1, which performs a grounding function, may be attached to at least one of the plurality of surfaces of the backing block 121 that is different from the surface thereof to which the connector 123 is attached.

The ground electrode 127-1 and the signal electrode 128, which are insulated from each other, may be attached to the piezoelectric layer 122 so as to surround the piezoelectric layer 122. The ground electrode 127-1 may perform the same functions as the ground layer 127 shown in FIG. 2. In one embodiment, the ground electrode 127-1 and the ground connector 124-1 may be electrically connected to perform a grounding function. The signal electrode 128 may be electrically connected to the plurality of pins 126 included in the connector 123. In one embodiment, the ground electrode 127-1 and the signal electrode 128 may be made of at least one conductive metal such as titanium (Ti), Chrome (Cr), aluminum (Al), copper (Cu), tin (Sn), nickel (Ni), gold (Au), silver (Ag), lead (Pb), and the like, or an alloy of the conductive metals, but are not limited thereto.

Figure 5:
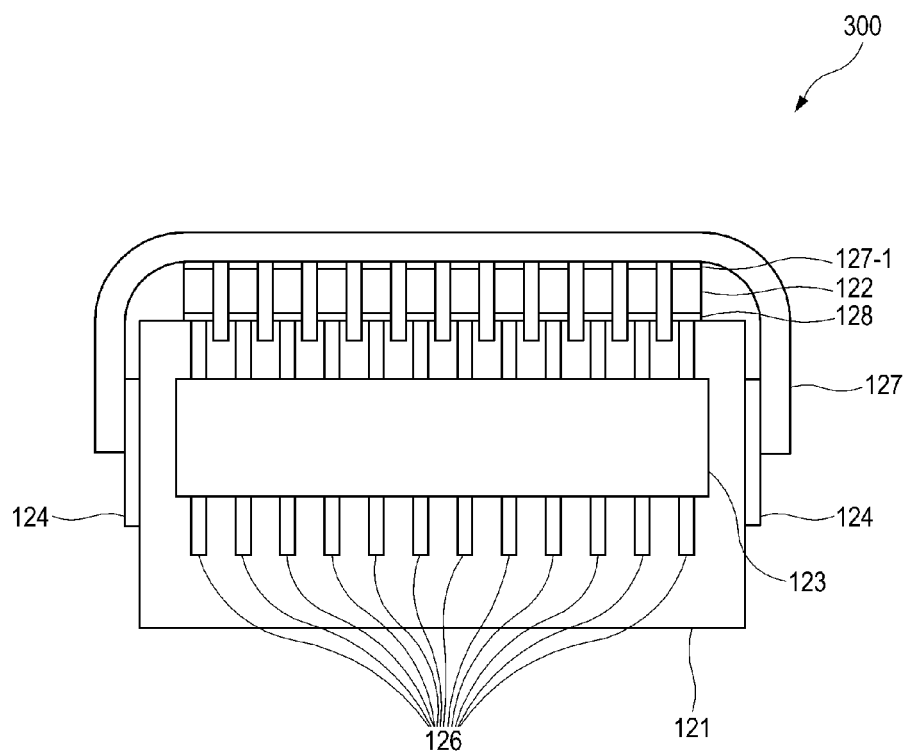
FIG. 5 is a lateral view showing an ultrasound transducer as viewed from one side according to an embodiment of the present disclosure.

FIG. 5 is a lateral view showing an ultrasound transducer 300 as viewed from one side according to an embodiment of the present disclosure.

As shown in FIG. 5, the ultrasound transducer 300 may include the backing block 121, the piezoelectric layer 122, the connector 123, the ground region 124, the ground layer 127, the ground electrode 127-1 and the signal electrode 128, and the connector 123 may include the plurality of pins 126. The elements that perform the same functions as those of the ultrasound transducers 120, 200 shown in FIG. 2-4 are denoted by the same reference numerals, and a detailed description thereof will be omitted.

The signal electrode 128 may be arranged at the bottom of the piezoelectric layer 122 and the ground electrode 127-1 may be arranged at the top of the piezoelectric layer 122. The ground electrode 127-1 may be connected to the ground region 124 of the backing block 124 via the ground layer 127. In one embodiment, the ground layer 127 may wrap the piezoelectric layer 122, the backing block 121 and a part of the ground region 124 and may be attached at the top of the ground electrode 127-1 in the shape of a ground return shield.

Figure 6:
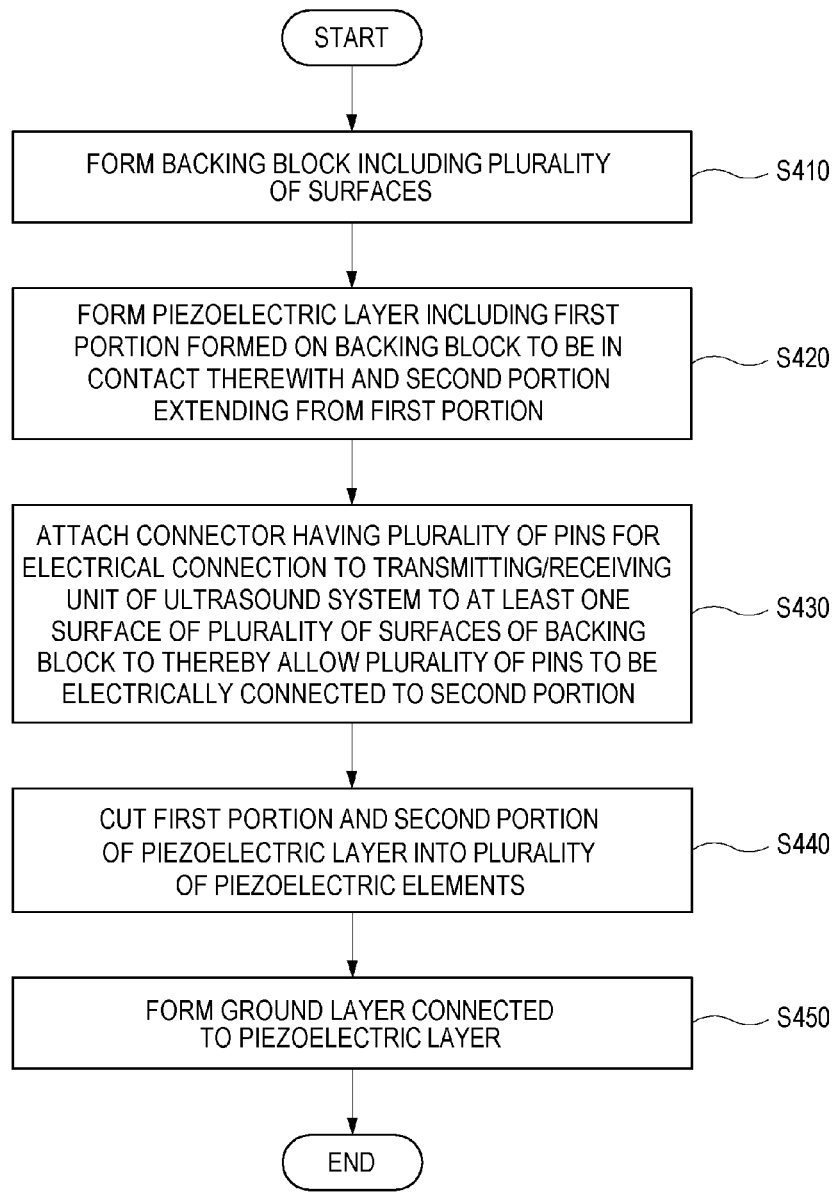
FIG. 6 is a flowchart showing a method of manufacturing an ultrasound transducer according to an embodiment of the present disclosure.

FIG. 6 is a flowchart showing a method of manufacturing an ultrasound transducer according to an embodiment of the present disclosure. Although process steps, method steps, algorithms, or the like are described in a particular sequential order, such processes, methods, and algorithms may be configured to work in any suitable order. In other words, the steps of the processes, methods, and algorithms described in various embodiments herein do not necessarily indicate that the steps are to be performed in the order described herein. Further, although some steps are described as being performed non-simultaneously, such steps may be performed simultaneously in other embodiments. Further, the illustration of a process by its depiction in a drawing does not imply that the illustrated process is exclusive of other variations and modifications thereto, that the illustrated process or any of its steps are necessary to one or more embodiments among the various embodiments, or that the illustrated process is preferred.

As shown in FIG. 6, in operation S410, a backing block including a plurality of surfaces may be formed. For example, referring to FIGS. 1 to 5, the backing block 121 including the plurality of surfaces having various shapes according to the shape of the ultrasound transducer 120 may be formed. In one embodiment, the backing block 121 may be formed of a material (e.g., a polymer resin) having an impedance value similar to the acoustic impedance of the plurality of piezoelectric elements 122-3 included in the piezoelectric layer 122 and having a high damping coefficient. In another embodiment, the backing block 121 may be formed by mixing an oxide of a metal such as chromium (Cr), iron (Fe), copper (Cu), and the like in a predetermined ratio with a material having a high damping coefficient.

In operation S420, a piezoelectric layer including a first portion formed on the backing block so as to be in contact therewith and a second portion extending from the first portion may be formed. For example, referring to FIGS. 1 to 5, the piezoelectric layer 122 including the first portion 122-1 formed on the backing block 121 to be in contact therewith and the second portion 122-2 extending from the first portion 122-1 may be formed in consideration of the shape of the backing block 121. In one embodiment, the piezoelectric layer 122 may be formed on the backing block 121 using an epoxy adhesive or the like.

In operation S430, a connector having a plurality of pins for electrical connection to the transmitting unit and the receiving unit of an ultrasound system is attached to at least one surface of the plurality of surfaces of the backing block so that the plurality of pins may be electrically connected to the second portion. For example, referring to FIGS. 1 to 5, the connector 123 having the plurality of pins 126 for electrical connection with the transmitting unit 110 and the receiving unit 130 of the ultrasound system 100 may be attached to at least one surface of the plurality of surfaces of the backing block 121 so that the plurality of pins 126 may be electrically connected to the second portion 122-2. In one embodiment, at least one conductive paste 125 selected from among a solder paste, an epoxy adhesive, and a silver epoxy may be used for the electrical connection between the plurality of pins 126 and the second portion 122-2, but is not limited thereto.

In operation S440, the first portion and the second portion of the piezoelectric layer may be cut into a plurality of piezoelectric elements. For example, referring to FIGS. 1 to 5, the first portion 122-1 and the second portion 122-2 of the piezoelectric layer 122 may be cut into the plurality of piezoelectric elements 122-3. Each of the plurality of piezoelectric elements 123 that have been cut may be connected to a corresponding one of the plurality of pins 126 of the connector 123. In one embodiment, when the first portion 122-1 and the second portion 122-2 of the piezoelectric layer 122 are cut into the plurality of piezoelectric elements 122-3, the conductive paste 125 attached between the second portion 122-2 and the plurality of pins 126 may be cut simultaneously, and a part of the backing block 121 that is connected to the conductive paste 125 may also be cut simultaneously.

In operation S450, a ground layer connected to the piezoelectric layer may be formed. For example, referring to FIGS. 1 to 5, the ground layer 127 connected to the piezoelectric layer 122 may be formed. In one embodiment, the ground layer 127 may be formed on the piezoelectric layer 122, and the ground electrode 127-1 and the signal electrode 128 may be insulated from each other and attached to the piezoelectric layer 122 so as to surround the piezoelectric layer 122. In this case, the ground electrode 127-1 may perform the same functions as the ground layer 127.

The above method has been described through specific embodiments, but the above method can be realized as computer-readable code on a computer-readable recording medium. The computer-readable recording medium includes all types of recording devices on which data that can be read by a computer system can be recorded in a computer-readable manner. For example, the computer-readable recording medium includes a ROM, a RAM, a CD-ROM, a magnetic tape, a floppy disk, an optical data storage device, and a carrier wave, such as data transmission through the Internet. Further, the computer-readable recording medium, which can be read by a computer, can be distributed over a plurality of computer systems that are connected to one another by a network such that code that can be read by a computer can be stored and executed in a decentralized manner. In addition, functional programs, code, and code segments for implementing the above embodiments can be easily inferred by programmers skilled in the art to which the present disclosure pertains.

While the present disclosure has been described in relation to various embodiments thereof, it should be appreciated that various modifications or changes may be made thereto, without departing from the spirit and scope of the present disclosure. It is, therefore, contemplated that the following claims should be interpreted so as to include all such equivalent structures as might be included within the spirit and scope of the present invention.

What is claimed is:

1. A method of manufacturing an ultrasound transducer, comprising:
   forming a backing block including a plurality of surfaces;
   forming a piezoelectric layer including a first portion formed on the backing block to be in contact therewith and a second portion extending from the first portion;
   electrically connecting a plurality of pins to the second portion by attaching a connector having the plurality of pins for electrical connection with at least one of a transmitting unit or a receiving unit of an ultrasound system to at least one surface of the plurality of surfaces of the backing block;
   cutting the first portion and the second portion of the piezoelectric layer into a plurality of piezoelectric elements, wherein each of the plurality of piezoelectric elements is connected to a corresponding one of the plurality of pins of the connector; and
   forming a ground layer connected to the piezoelectric layer.

2. The method of manufacturing an ultrasound transducer of claim 1, wherein electrically connecting the plurality of pins to the second portion includes electrically connecting the plurality of pins of the connector to the second portion of the piezoelectric layer by attaching at least one conductive paste selected from among a solder paste, an epoxy adhesive, and a silver epoxy between the second portion and the plurality of pins.

3. The method of manufacturing an ultrasound transducer of claim 2, wherein cutting the first portion and the second portion of the piezoelectric layer into the plurality of piezoelectric elements includes simultaneously cutting the conductive paste attached between the second portion and the plurality of pins when cutting the first portion and the second portion of the piezoelectric layer into the plurality of piezoelectric elements.

4. The method of manufacturing an ultrasound transducer of claim 1, wherein cutting the first portion and the second portion of the piezoelectric layer into the plurality of piezoelectric elements includes inserting an insulating material between each pair of adjacent piezoelectric elements.

5. The method of manufacturing an ultrasound transducer of claim 1, wherein the second portion protrudes from the first portion by a length greater than or equal to a height of the plurality of pins of the connector.

6. The method of manufacturing an ultrasound transducer of claim 1, wherein forming the backing block includes forming a ground region on one or more surfaces of the backing block for connecting to the ground layer.

7. The method of manufacturing an ultrasound transducer of claim 1, wherein forming the ground layer connected to the piezoelectric layer includes forming the ground layer on the piezoelectric layer.

8. The method of manufacturing an ultrasound transducer of claim 1, wherein forming the ground layer connected to the piezoelectric layer includes:
   attaching a ground connector configured to perform a grounding function to at least one of surfaces of the backing block that is different from the surface to which the connector is attached; and
   connecting the ground layer and the ground connector.

9. An ultrasound transducer comprising:
   a backing block including a plurality of surfaces;
   a piezoelectric layer including a first portion formed on the backing block to be in contact therewith and a second portion extending from the first portion;

a connector having a plurality of pins for electrically connecting to at least one of a transmitting unit or a receiving unit of an ultrasound system, the connector being attached to at least one surface of the plurality of surfaces of the backing block and the plurality of pins being configured to electrically connect to the second portion; and a ground layer connected to the piezoelectric layer, wherein the piezoelectric layer includes a plurality of piezoelectric elements that are cut in the first portion and the second portion, and each of the plurality of piezoelectric elements is connected to a corresponding one of the plurality of pins of the connector.

10. The ultrasound transducer of claim 9, wherein at least one conductive paste selected from among a solder paste, an epoxy adhesive, and a silver epoxy is attached between the second portion and the plurality of pins, so that the plurality of pins of the connector is electrically connected to the second portion of the piezoelectric layer.

11. The ultrasound transducer of claim 9, wherein the conductive paste attached between the second portion and the plurality of pins is cut simultaneously with cutting the first portion and the second portion of the piezoelectric layer into the plurality of piezoelectric elements.

12. The ultrasound transducer of claim 9, wherein, an insulating material is disposed between each pair of adjacent piezoelectric elements.

13. The ultrasound transducer of claim 9, wherein the second portion protrudes from the first portion by a length greater than or equal to a height of the plurality of pins of the connector.

14. The ultrasound transducer of claim 9, wherein the backing block includes a ground region formed on one or more surfaces of the backing block and configured to be connected to the ground layer.

15. The ultrasound transducer of claim 14, wherein the ground region includes a ground connector configured to perform a grounding function and attached to at least one of surfaces of the backing block that is different from the surface to which the connector is attached.

16. The ultrasound transducer of claim 9, wherein the ground layer is formed on the piezoelectric layer.

* * * * *